US008073148B2

(12) United States Patent
Kim

(10) Patent No.: US 8,073,148 B2
(45) Date of Patent: Dec. 6, 2011

(54) SOUND PROCESSING APPARATUS AND METHOD

(75) Inventor: Hyun-Soo Kim, Yongin-si (KR)

(73) Assignee: Samsung Electronics Co., Ltd. (KR)

( * ) Notice: Subject to any disclaimer, the term of this patent is extended or adjusted under 35 U.S.C. 154(b) by 1557 days.

(21) Appl. No.: 11/479,472

(22) Filed: Jun. 30, 2006

(65) Prior Publication Data

US 2007/0010997 A1 Jan. 11, 2007

(30) Foreign Application Priority Data

Jul. 11, 2005 (KR) ........................ 10-2005-0062465
Dec. 8, 2005 (KR) ........................ 10-2005-0119625

(51) Int. Cl.
*A61F 11/06* (2006.01)

(52) U.S. Cl. ..................... 381/71.1; 381/94.1; 381/94.2; 704/226; 704/205; 704/207

(58) Field of Classification Search ................. 381/71.1, 381/73.1, 94.1, 94.2, 102, 107; 704/205, 704/207, 208, 216, 234, 226
See application file for complete search history.

(56) References Cited

U.S. PATENT DOCUMENTS 5,228,088 A 7/1993 Kane et al.
5,490,231 A 2/1996 Kane et al.
5,491,836 A 2/1996 Neiss
5,617,450 A * 4/1997 Kakuishi et al. .............. 375/230
5,619,565 A 4/1997 Cesaro et al.
5,687,285 A * 11/1997 Katayanagi et al. .......... 704/226
5,982,901 A * 11/1999 Kane et al. ....................... 381/13
6,154,547 A * 11/2000 Whitecar ..................... 381/94.2
6,173,256 B1 1/2001 Gigi
6,351,731 B1 * 2/2002 Anderson et al. ............. 704/233
6,975,674 B1 * 12/2005 Phanse et al. ................. 375/219
6,987,992 B2 * 1/2006 Hundal et al. ............. 455/569.1
7,289,626 B2 * 10/2007 Carter et al. ............. 379/387.02
7,426,250 B2 * 9/2008 Chen ............................. 375/345
2002/0097884 A1 * 7/2002 Cairns .......................... 381/71.4
2005/0114117 A1 * 5/2005 Kristjansson et al. ........ 704/205
2005/0195994 A1 * 9/2005 Saito et al. ..................... 381/102
2008/0267424 A1 * 10/2008 Mori et al. ................... 381/94.1

FOREIGN PATENT DOCUMENTS

KR 1020000069831 11/2000
KR 1020020022257 3/2002
WO WO 02/45075 6/2002
WO WO 2005/045808 5/2005

OTHER PUBLICATIONS

Kobatake, "Enhancement of Noisy Speech by Maximum Likelihood Estimation", 1991, IEEE, pp. 973-976.*

(Continued)

*Primary Examiner* — Vivian Chin
*Assistant Examiner* — Friedrich W Fahnert
(74) *Attorney, Agent, or Firm* — The Farrell Law Firm, P.C.

(57) ABSTRACT

Disclosed is an apparatus and method for processing signals such as sound signals. The sound processing apparatus includes a sound signal input unit for receiving sound signals, a harmonic noise separator for separating a harmonic region and a noise region from the received sound signals, a noise restraint index determination unit for determining an optimal noise restraint index k according to a system and circumstance, and a noise restrainer for restraining the separated noise region depending on the noise restraint index k so as to output noise attenuated signals.

16 Claims, 6 Drawing Sheets

OTHER PUBLICATIONS

Hardwick J et al, "Speech Enhancement Using the Dual Excitation Speech Model", Statistical Signal and Array Processing, vol. 4, Apr. 27, 1993.

Kobatake H et al, "Enhancement of Noisy Speech by Maximum Likelihood Estimation", vol. 2 Conf. 16, Apr. 14, 1991.

* cited by examiner

SOUND PROCESSING APPARATUS AND METHOD

PRIORITY

This application claims priority to applications entitled "Sound Processing Apparatus and Method" filed in the Korean Intellectual Property Office on Jul. 11, 2005 and assigned Ser. No. 2005-62465, and on Dec. 8, 2005 and assigned Ser. No. 2006-119625, the contents of each of which are incorporated herein by reference.

BACKGROUND OF THE INVENTION

1. Field of the Invention

The present invention relates to a sound processing apparatus and method, and more particularly, to a sound processing apparatus and method which can efficiently attenuate noise according to a real time environment.

2. Description of the Related Art

Typically, in the field of sound signal processing, noise reduction is one of the most important issues to consider. Unfortunately, it is also one of the most difficult issues to solve.

Although conventional noise processing algorithms are applied using predetermined methods which take into account an expected noise elimination effect, they do not take into account their flexibility and utility with respect to various types of noise and circumstances. Rather, most conventional noise processing methods employ algorithms which use filtering methods that are assumed without respect to their application. Further, although conventional noise processing methods can process noise under various assumptions, they often fail to adequately process noise in many typical cases in which such assumptions are not suitable. Thus, few commercially available noise removal algorithms are applicable to filtering noise that exists in a real environment.

SUMMARY OF THE INVENTION

Accordingly, the present invention has been made to solve the above-mentioned problems occurring in the prior art, and an object of the present invention is to provide a sound processing apparatus and method, which can efficiently attenuate and/or remove noise from signals transmitted in various circumstances.

Another object of the present invention to provide a sound processing apparatus and method, which can accurately separate a harmonic region and a non-harmonic region from sound signals.

In accordance with an aspect of the present invention, there is provided a sound processing apparatus which includes a sound signal input unit for receiving sound signals, a harmonic noise separator for separating a harmonic region and a noise region from the received sound signals, and a noise restrainer for restraining the separated noise region depending on the noise restraint index k so as to output noise attenuated signals.

In accordance with an aspect of the present invention, there is provided a sound processing method which includes separating a harmonic region and a noise region from sound signals, and restraining the separated noise region depending on the noise restraint index k so as to output noise attenuated signals.

In accordance with yet another aspect of the present invention, there is provided a sound processing apparatus, which includes a sound signal input unit for receiving sound signals, a harmonic noise separator for repeatedly amplifying a harmonic region and attenuating a noise region in the received sound signals until an energy difference between two continuous harmonic components is lowered below a predetermined threshold value, while separating the harmonic region and the noise region when the energy difference between the two continuous harmonic components is lowered below the preset thresholdvalue; and a noise restrainer for restraining the separated noise region depending on a noise restraint index k so as to output noise attenuated signals.

In accordance with a further aspect of the present invention, there is provided a sound processing method, which includes repeatedly amplifying an of a harmonic region and attenuating a noise region in received sound signals until an energy difference between two continuous harmonic components is lowered below a threshold value which is already set, separating the harmonic region and the noise region when the energy difference between the two continuous harmonic components is lowered below the predetermined threshold value after the amplification of the harmonic region and the reduction of the noise region are performed, and restraining the separated noise region depending on a noise restraint index k so as to output noise attenuated signals.

According to the present invention, an algorithm, for optimally processing noise according to need regardless of any assumptions relating to circumstance, signal, and type of noise, can be applied to a sound signal processing system including sound coding, sound synthesizing, and sound recognition.

The present invention provides a method of separating a harmonic region and a noise region, and using an optimal parameter so as to restrain noise with respect to the noise region. The optimal parameter used for restraining noises may be set as required for optimal system configuration. The system may also automatically set the optimal parameter depending on circumstance. For example, actual sound signals, such as a user's voice signal, may include various and unexpected types of noise, which can generally be classified as all types of sounds excluding the user's voice. Although typical sound processing methods using a particular the conventional noise processing algorithm may fail to process noise when the noise attenuating algorithm is not suitable for the circumstances, the present invention overcomes this deficiency by properly selecting an appropriate noise attenuating algorithm according to situation and circumstances. Thus, ensuring that noise is properly attenuated regardless of its type and/or transmission method. Therefore, the present invention provides a system and method for processing sounds that can be flexibly and widely adapted to every system relating to the sounds, and is simple and robust (against noise) and can optimally attenuate noise.

BRIEF DESCRIPTION OF THE DRAWINGS

The above and other objects, features, and advantages of the present invention will be more apparent from the following detailed description taken in conjunction with the accompanying drawings, in which.

DETAILED DESCRIPTION OF THE PREFERRED EMBODIMENT

Hereinafter, a preferred embodiment of the present invention will be described with reference to the accompanying drawings. In the following description of the present invention, a detailed description of known functions and configurations incorporated herein is omitted to avoid making the subject matter of the present invention unclear.

The present invention discloses a sound processing apparatus having a structure in that sound signals are divided into a harmonic region and a noise region while the noise region is restrained according to a noise restraint index adapted to a system or circumstances in which a noise and the signal continuously change.

Figure 1:
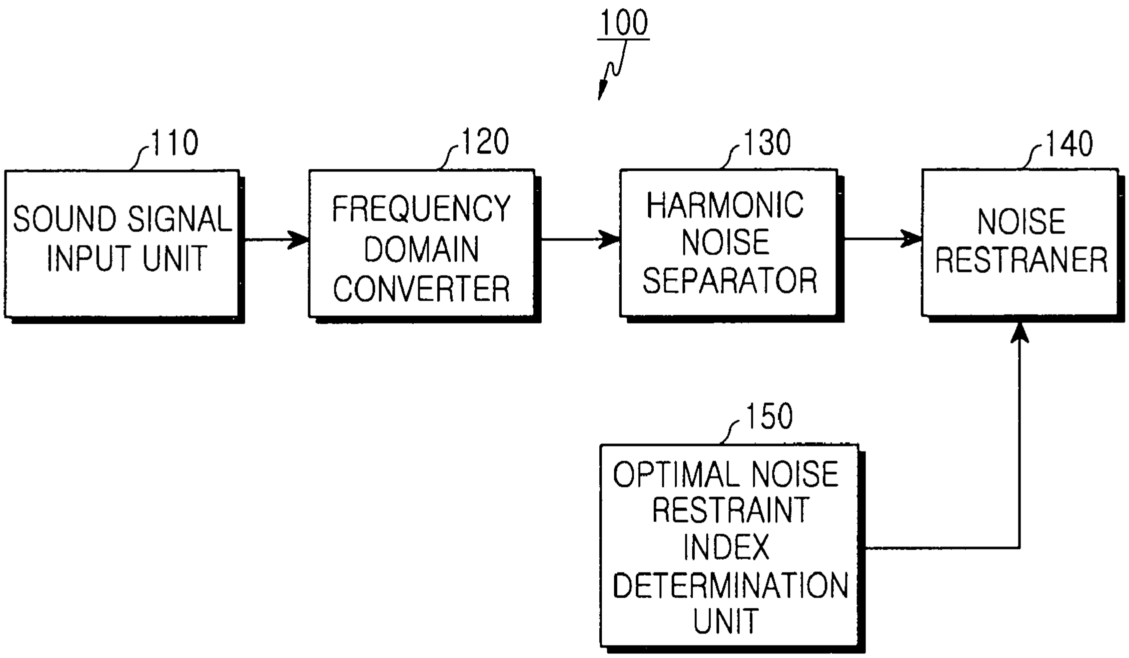
FIG. 1 is a block diagram illustrating a sound processing apparatus according to the present invention.

FIG. 1 is a block diagram illustrating the sound processing apparatus according to the present invention.

Referring to FIG. 1, the sound processing apparatus according to the present invention includes a sound signal input unit 110, a frequency domain converter 120, a harmonic noise separator 130, a noise restrainer 140 and an optimal noise restraint index determination unit 150.

The sound signal input unit 110 includes a microphone (or the like) through which sound signals may be input. The frequency domain converter 120 converts the input sound signals of a time domain into the sound signals of a frequency domain. The frequency domain converter 120 coverts the sound signals in the time domain into the sound signals in the frequency domain using, for example, a Fast Fourier Transform (FFT).

The harmonic noise separator 130 receives signals made in such a manner that the frequency domain converter 120 selects a predetermined length of a sample frame from a residual signal for a linear prediction in the input sound signals and converts the sample frame into a predetermined frequency domain.

Figure 4:
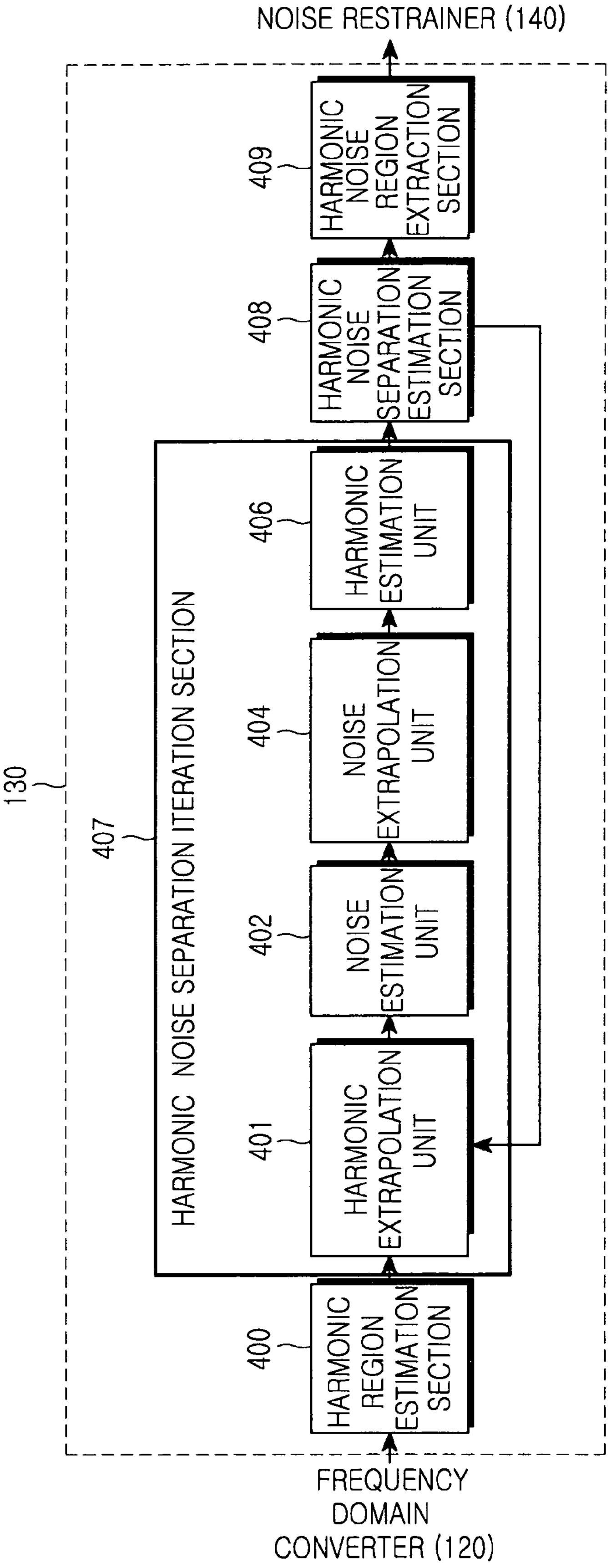
FIG. 4 is a block diagram illustrating an inner structure of a harmonic-noise separator in the sound processing apparatus according to the present invention.

Hereinafter, the structure and operation of the harmonic noise separator 130 which divides sounds signals into a harmonic region and a noise region according to the present invention will be described in detail with reference to FIG. 4. The harmonic noise separator 130 according to the present invention may include a harmonic noise separation-iteration section 407 which may include one or more a harmonic region estimation unit 400, a harmonic extrapolation unit 401, a noise estimation unit 402, a noise extrapolation unit 404, and a harmonic estimation unit 406, a harmonic noise separation estimation section 408, and a harmonic noise region extractor 409 for extracting harmonic noise region.

First, the harmonic region estimation unit 400 determines a harmonic domain using information relating to cepstrum and pitch when the sound signals, which are converted into the frequency domain by means of the frequency domain converter 120, are inputted therein.

Figure 2:
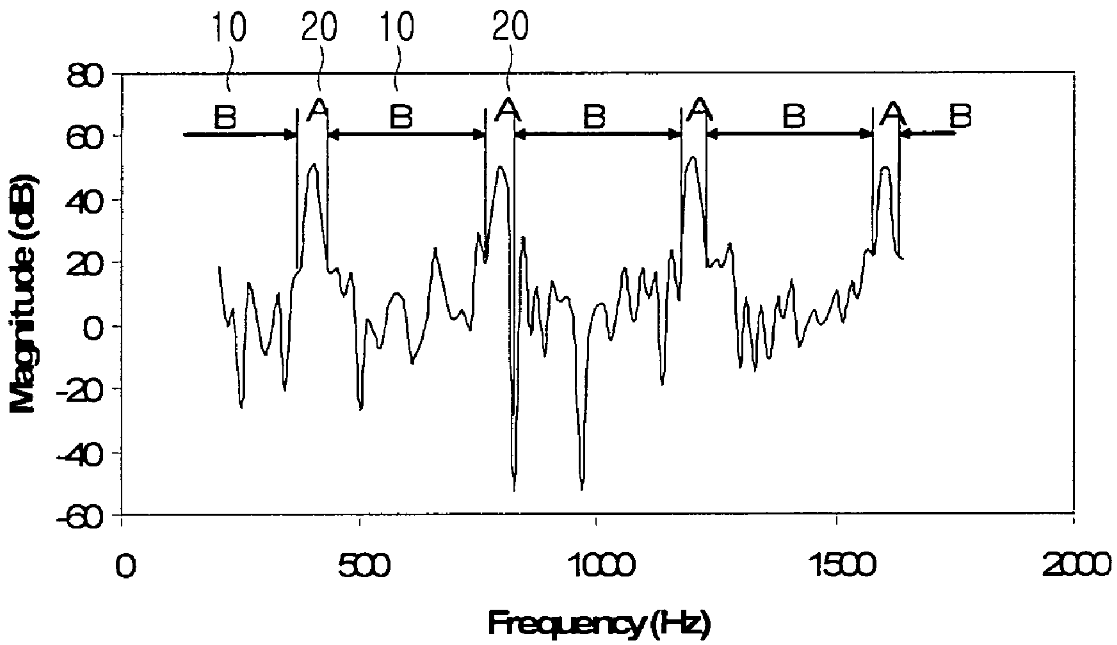
FIG. 2 is a graph illustrating sound signals on a frequency domain.

Next, the sound signals in the frequency domain will be described with reference to FIG. 2, which is a graph illustrating the sound signals in the frequency domain. Referring to FIG. 2, the sound signals can be divided into a noise region B 10 and a harmonic region A 20. Conventionally, as noises are filtered from the sound signals according to the magnitude of the noises in the sound signals, the harmonic region A 20 also is restrained so as to have an effect on the quality of the sound signals. However, according to the present invention, the noise is restrained only in the noise region excluding the harmonic region.

Here, provided that the sound signals is referred to as x(n), the harmonic region is indicated by h(n), and the noise region is referred to as w(n), the sound signal can be defined by Equation (1) below.

$$x(n)=h(n)+w(n) \quad \text{Equation (1)}$$

Meanwhile, the harmonic noise separation iteration section 407 performs interpolation and extrapolation for the harmonic region and the noise region until the harmonic region and the noise region are accurately separated from each other. As discussed above, the harmonic noise separation iteration section 407 may include the harmonic extrapolation unit 401, the noise estimation unit 402, the noise extrapolation unit 404, and the harmonic estimation unit 406.

The harmonic extrapolation unit 401 sets values (for example a Discrete Fourier Transformer (DFT) value) of the frequency domain in the noise region excluding the harmonic region, which is determined by the harmonic region estimation unit 400, to zero.

The noise estimation unit 402 extrapolates the current harmonic or sinusoidal samples in the harmonic or sinusoidal regions in the noise region. The sinusoidal region is a section where a sinusoidal component exists, and has a broader meaning than a harmonic region. A sinusoidal component is a part of a voice signal (having a periodicity) which can be expressed as a sinusoidal representation such as sin, cos. A harmonic sample in the noise region is subtracted from an initial noise sample, while the residual noise sample estimations are extrapolated into the harmonic or sinusoidal region.

At this time, the initial noise sample refers to a linear prediction residual spectrum in the noise region.

In the meantime, the noise extrapolation unit 404 sets values of the frequency domain in the harmonic region, for example DFT values, to zero.

The harmonic estimation unit 406 extrapolates the current noise samples in the noise region into the harmonic region. The noise sample in the harmonic region is subtracted from the initial harmonic samples having been subjected to the harmonic region interpolation in the way described above, and the residual harmonic sample estimations are then extrapolated into the noise region.

At this time, the initial harmonic sample refers to the linear prediction residual spectrum in the harmonic region.

As described above, the harmonic noise separation iteration section 407 amplifies the harmonic signals of the harmonic region in the frequency domain, and operates to decrease the noise signals in the noise region.

Then, when the harmonic signals of the harmonic region are amplified in the frequency domain of the sound signals inputted as described above while the noise signals in the noise region decrease, the harmonic noise separation estimation section 408 determines if an energy difference between two continuous harmonic components is below a preset thresholdvalue. Further, until the energy difference between the two continuous harmonic components is lowered below the preset thresholdvalue, the harmonic noise separation estimation section 408 enables the harmonic extrapolation unit 401, the noise estimation unit 402, the noise extrapolation unit 404, and the harmonic estimation unit 406 to continuously repeat their operations, based on the estimation result, thereby amplifying the harmonic region and decreasing the noise region. Further, as the result of estimation, when the energy difference between the two continuous harmonic components is lowered below the preset thresholdvalue, the harmonic noise separation estimation section 408 separates the harmonic region and the noise region which are divided according to the amplification and the decrease in the harmonic noise region extraction section 409, and then provides the harmonic noise region to the noise restrainer 140.

Figure 6A:
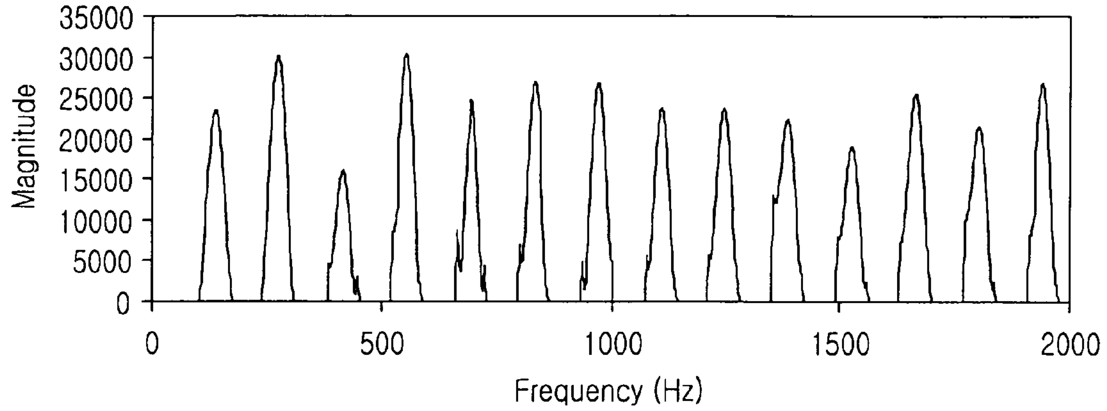
FIGS. 6A and 6B are graphs respectively illustrating divided signals of a harmonic region and a noise region according to the present invention.
Figure 6B:
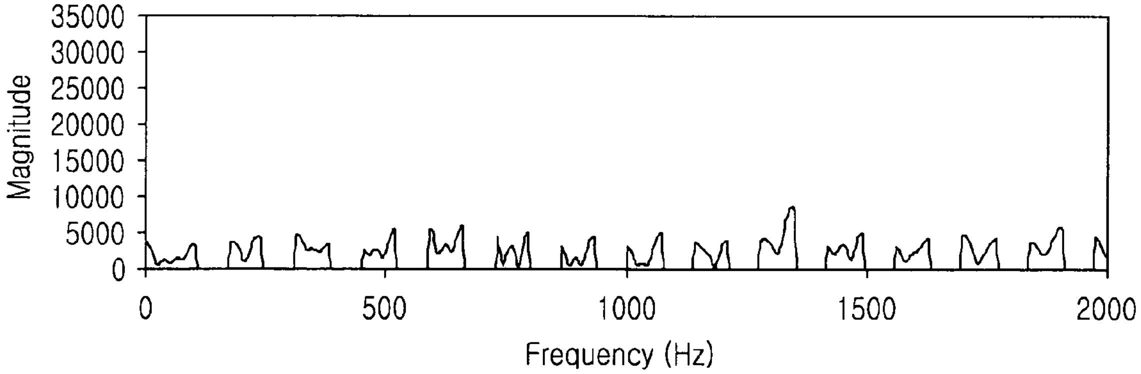

FIGS. 6A and 6B are graphs respectively illustrating divided sound signals in the harmonic region and the noise region of the frequency domain, which are separated through the harmonic noise region extraction section 409 according to the present invention. Referring to FIG. 6A a harmonic component including the harmonic region is shown. Referring to FIG. 6B a non-harmonic component including the noise region is shown. It is noted that the sound signals can be accurately separated as indicated by FIGS. 6A and 6B when the sound signals are processed by the harmonic noise separator 103 according to the present invention. The method of dividing the sound signals into the harmonic region and the noise region in the frequency domain according to the present invention can be widely used for coding, synthesizing, and reinforcement systems using all of sound signals and audio signals.

When the harmonic noise region is separated through the harmonic noise separator 130, the noise restrainer 140 restrains noise in the noise region using the noise restraint index k according to a system having the sound processing apparatus, or its characteristics.

Provided that signals in which the noise is reduced with respect to the noise region by the noise restrainer 140 using the optimal restraint index are $\bar{x}$, the noise reduced signals can be defined by Equation (2) below.

$$\bar{x}=K(h+kw)\equiv KX \quad \text{Equation (2)}$$

wherein, $\bar{x}$ indicates the noise reduced signals, k is the optimal noise restraint index used for optimally restraining noise according to a system having the sound processing apparatus or its characteristic, h is the harmonic region, and w indicates the noise region. K is a coefficient constant for representing a noise-removed signal and can be calculated by the following Equation (2a) according to a method of the present invention if k representing a degree of noise removing is determined:

$$K=\left(1-\frac{\beta}{2}\right)\frac{x^Tx}{X^Tx},\quad \bar{x}=KX \quad \text{Equation (2a)}$$

X is a signal that is made by a combination of h (harmonic component of an original signal) and kw (some non-harmonic component of the original signal being decreased). X itself is not a signal in which a noise is removed, but is combined with K and then becomes $\bar{x}$, signal in which a noise is removed.

The optimal noise restraint index determination unit 150 for determining an optimal noise restraint index determines the noise restraint index k. The noise restraint index indicates the extent of restraining the noise. Assuming that it is improper to forcibly restrain the noise, such as in the conventional art (i.e. in a low pass filter), because the component of the sound signal is involved in the frequency domain noise region (non-harmonic component), the present invention determines the noise restraint index k according to the system having the sound processing apparatus, or its characteristic.

Specifically, the present invention obtains the noise reduced signal $\bar{x}$ after determining k (the extent of noise reduction in the system) in the original signal x(n). In this case, the present invention applies two essential constraints as follows:

(1) a signal has identical energy before and after noise is removed, i.e., $\|\bar{x}\|^2=\|x\|^2$; and (2) a signal before noise is removed is substantially identical with a signal after noise is removed (i.e., $\|x-\bar{x}\|^2\leqq\beta\|x\|^2$ (herein, $\beta<1$, $k<1$).

The second constraint provides that the noise-removed signal should be similar to the original signal. That is, the original signal should not be distorted after noise remove processing. If the original signal is distorted through noise removing, information is lost. If so, there is no reason for the noise removing process. That is, if the original signal is distorted, information in a codec and recognizer etc. during the latter part of the noise removing process is lost. Consequently, it is difficult to expect a proper result.

When the above mentioned constraints are applied to sound signals of each frame in the form of vector, the sound signals can be defined by Equation (3) below:

$$\bar{x}^T\bar{x}=x^Tx,(x-\bar{x})^T(x-\bar{x})=\beta x^Tx \quad \text{Equation (3)}$$

Therefore, Equation (4) can be expressed.

$$\bar{x}^Tx=\left(1-\frac{\beta}{2}\right)x^Tx \quad \text{Equation (4)}$$

As described above, k (which is less than 1) is input according to the extent of noise reduction, and thus K can be obtained. As a result, the noise reduced signal x can also be obtained. The present invention can be easily applied to the harmonic region and the noise region after the harmonic region and the noise region are separated from the sound signal, and can be flexibly used to one skilled in the art. Specifically, the present invention is adaptively applicable according to the system and the circumstance, because it is possible to selectively use the optimal noise restraint index k according to the present invention.

Therefore, K and $\bar{x}$ can be defined by Equation (5).

$$K=\left(1-\frac{\beta}{2}\right)\frac{x^Tx}{X^Tx},\quad \bar{x}=KX \quad \text{Equation (5)}$$

The noise restrainer 140 restrains and outputs the noise region B 10 of the sound signals according to the obtained noise restraint index k. At this time, since the harmonic region and the noise region are respectively processed in order to securely separate the harmonic region and the noise region through the harmonic noise separator 130, the sound signals in which the noise is restrained output the signals respectively including the harmonic region and the restrained noise region.

Hereinafter, the method for processing the sounds according to the present invention will be described with reference to FIG. 3, which is a flow chart illustrating a sound processing method according to the present invention.

Figure 3:
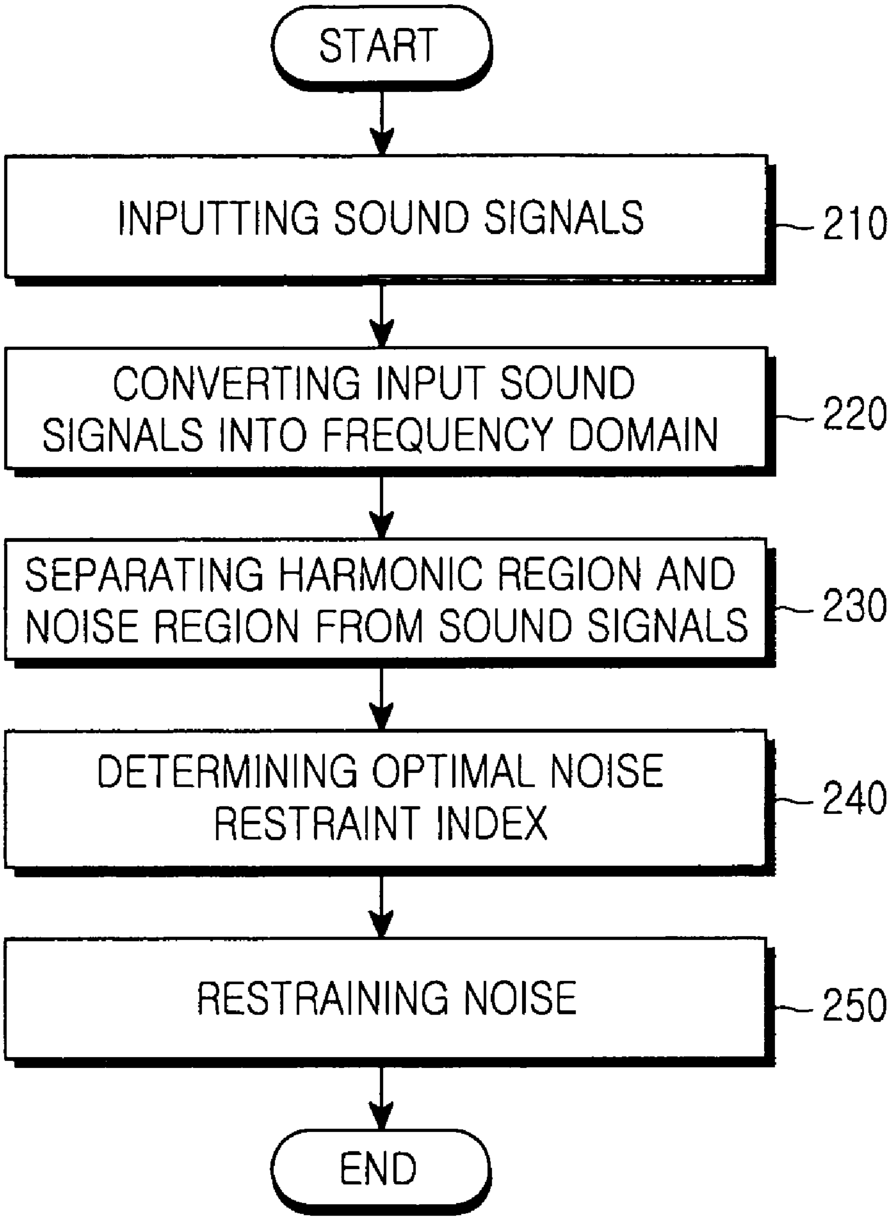
FIG. 3 is a flowchart illustrating a sound processing method according to the present invention.

Referring to FIG. 3, the sound signal input unit 110 of the sound processing apparatus 100 receives sound signals through, for example, a microphone (or other sound input means) at step 210. Then, the frequency domain converter 120 converts a sound signal in the time domain among the received sound signals into sound signal in the frequency domain using the Fast Fourier Transform (FFT) at step 220. Next, the harmonic noise separator 130 separates the harmonic region and the noise region from the sound signals of the frequency domain at step 230. The operation of separating the harmonic region and the noise region from the sound signals at the step 230 will be described in detail with reference to FIG. 5. The sound processing apparatus 100 determines the optimal noise restraint index k using the determination unit 150, at step 240. As described above, the noise restraint index indicates noise that is restrained. According to the present invention, it is assumed that it is improper to forcibly restrain the noise, because the component of the sound signals is included in the frequency domain noise region (non-harmonic component). Therefore, the present invention determines the noise restraint index k according to the system having the sound processing apparatus, or its characteristic.

Then, the sound processing apparatus 100 can restrain the noise region of the sound signals according to the optimal noise restraint index obtained at the step 240 so as to obtain the sound signals in which the noise is attenuated, at step 250.

Now, a process of separating the harmonic region and the noise region from the sound signals by using the harmonic noise separator 130 will be described in detail with reference to FIG. 5 which is a flow chart illustrating a method for performing the harmonic noise separation according to the present invention.

Figure 5:
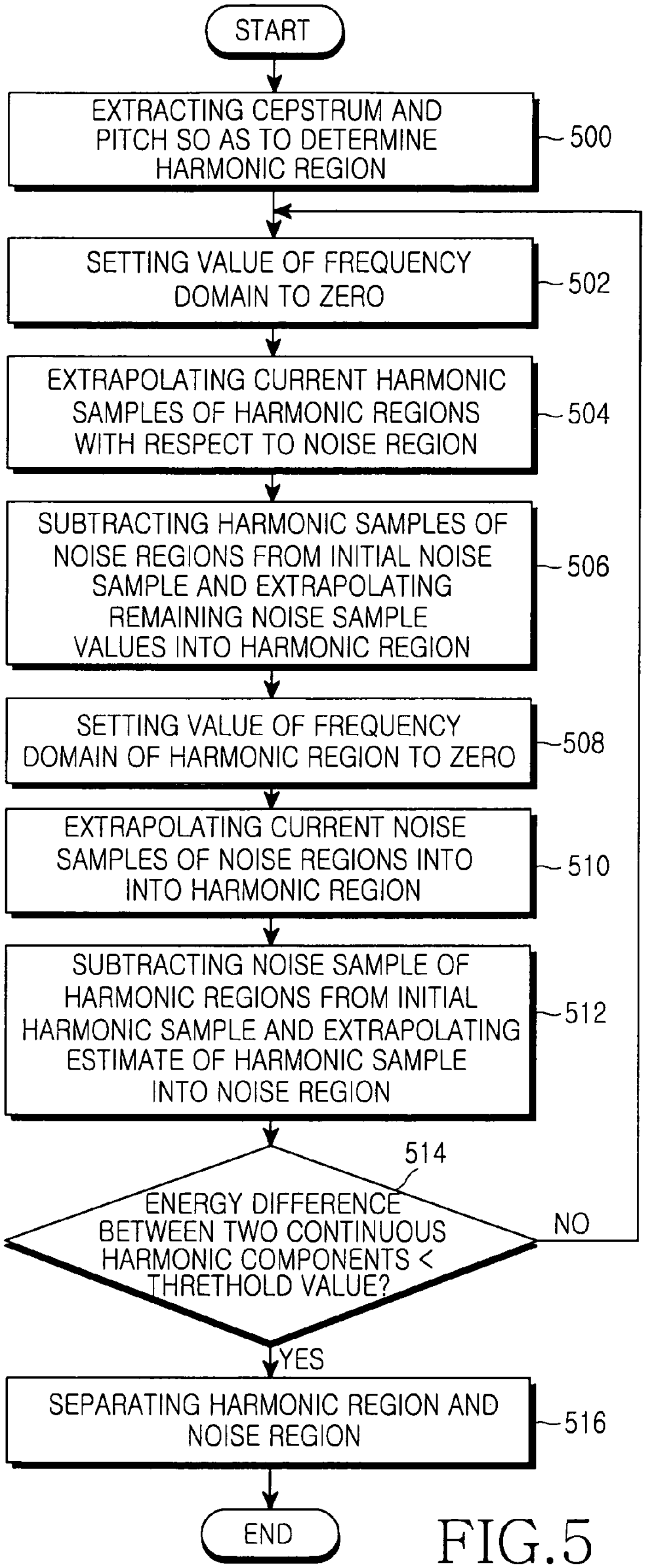
FIG. 5 is a flowchart illustrating a method for performing the harmonic-noise separation according to the present invention.

Referring to FIG. 5, when the sound signals which are converted into the frequency domain are input from the frequency domain converter 120 to the harmonic region estimation unit 400, the harmonic region estimation unit 400 estimates the harmonic region using information relating to cepstrum and pitch at step 500.

Then, the harmonic extrapolation unit 401 sets the frequency domain values in the noise region, which excludes the harmonic region estimated by the harmonic region estimation unit 400, to zero at step 502.

When the noise estimation unit 402 extrapolates the current harmonic or sinusoidal samples in the harmonic or sinusoidal regions into the noise region at step 504.

The noise estimation unit 402 subtracts the harmonic sample of the noise region from the initial noise sample extrapolated, and then extrapolates the residual noise sample estimations into the harmonic or sinusoidal region at step 506.

At this time, the initial noise sample refers to a linear prediction residual spectrum in the noise region.

Specifically, the sound processing apparatus 100 performs an operation of amplifying the sound signals in the harmonic region at steps 502, 504, and 506.

Next, the noise extrapolation unit 404 sets the value of the frequency domain of the harmonic region estimated by the harmonic region estimation section 400, for example DFT value, to zero at step 508, and the harmonic estimation unit 406 extrapolates the current noise samples of the noise region into the harmonic region at step 510. Then, the harmonic estimation unit 406 subtracts the noise sample of the harmonic region from the initial harmonic sample, and then extrapolates the residual harmonic sample estimations into the noise region, at step 512. At this time, the initial harmonic sample refers to the linear prediction residual spectrum of each harmonic region.

Specifically, the sound processing apparatus 100 performs an operation of reducing the sound signals of the noise region in the steps 508, 510, and 512.

Then, the sound processing apparatus 100 amplifies the sound signal of the harmonic region among the input sound signals through the steps 502 to 512, and reduces the sound signal in the noise region, which in turn progresses toward step 514.

The harmonic noise separation estimation section 400 then determines if the energy difference between two continuous harmonic components is lowered below a preset threshold value at step 514. The preset threshold value can be set by a user according to the system. Hence, it is not obtained by calculation, but determined by histogram or statistical analysis.

As a result, if it is determined at the step 514 that the energy difference between the two continuous harmonic components is lower than the preset thresholdvalue, the harmonic noise region extraction section 409 separates the harmonic region and the noise region from each other according to the amplification and reduction and then provides each harmonic noise region to the noise restrainer 140, at step 516.

However, if it is determined at the step 514 that the energy difference between the two continuous harmonic components is greater than the thresholdvalue, the steps 502 to 512 are repeated so as to amplify the harmonic region and to reduce the noise region until the energy difference between the two continuous harmonic components is lower than the preset thresholdvalue.

The algorithm disclosed by the present invention can be applied to sound processing systems and can be used for processing sound signals for speech enhancement.

For example, in the case of sound coding, sound synthesizing, and sound recognition algorithm, an optimal noise restraint index k can be easily inserted into a pre-processor of a system and can be either appointed according to requirements and specifications of the system or adaptively input into a sound processing system, so that the sound processing system can use a noise reduced signal x as an input signal. Specifically, in the case where various types of noises can occur due to the characteristics of a system (i.e., the characteristics of a portable terminal and/or its telematics such as, movement), conventional noise processing methods cannot optimally process noises in consideration of an unpredictable circumstance, but the sound processing algorithm of the present invention can reduce the noise by allowing the system to determine the extent of processing noise. In addition, the sound processing algorithm of the present invention can be easily inserted into the sound processing system, so as to improve the efficiency of the system. Further, when the sound processing algorithm according to the present invention is inserted into post-processing, noise can be easily attenuated and/or removed, thereby improving the quality of sound. The sound processing algorithm itself is very flexible, and can be applied to various fields.

The present invention can solve the problem which is most important in a system relating to sound processing including sound recognition so as to determine the level of the noise reduction adapted to a users' desire, thereby realizing the optimal capability according to the system.

While the invention has been shown and described with reference to a certain preferred embodiment thereof, it will be understood by those skilled in the art that various changes in form and details may be made therein without departing from the spirit and scope of the invention as defined by the appended claims.

What is claimed is:

1. A sound processing apparatus, comprising:

a sound signal input unit for receiving sound signals;

a harmonic noise separator for separating a harmonic region and a noise region from the received sound signals; and a noise restrainer for restraining the separated noise region depending on a predetermined noise restraint index k so as to output noise attenuated signals, wherein the noise attenuated signals are obtained using first and second constraints which respectively assume that signals have substantially the same energy both before and that after noise is processed, and signals after noise is processed are substantially identical to signals before the noise is processed.

2. The sound processing apparatus as claimed in claim 1, wherein the harmonic noise separator uses information corresponding to pitch of the received sound signals.

3. The sound processing apparatus as claimed in claim 1, wherein the sound signals x(n) include the harmonic region h(n) and the noise region w(n) as defined by x(n)=h(n)+w(n).

4. The sound processing apparatus as claimed in claim 1, wherein the first and second constraints are applied to the sound signals in the form of vector as defined by $$\bar{x}^T\bar{x}=x^Tx,(x-\bar{x})^T(x-\bar{x})=\beta x^Tx,$$

and arranged as represented by $$\bar{x}^T x=\left(1-\frac{\beta}{2}\right)x^T x,$$

so that the noise restraint index defined by $$K=\left(1-\frac{\beta}{2}\right)\frac{x^T x}{X^T x},$$
$$\bar{x}=KX,$$

is obtained, and wherein β is a constant less than 1.

5. A sound processing method, comprising the steps of:

separating a harmonic region and a noise region from sound signals; and restraining the separated noise region depending on a predetermined noise restraint index so as to output noise attenuated signals, wherein the noise attenuated reduced signals are obtained using first and second constraints which respectively assume that signals have substantially the same energy both before and after noise is processed, and signals after noise is processed are substantially identical to signals before the noise is processed.

6. The sound processing method as claimed in claim 5, wherein the harmonic noise separator uses information corresponding to pitch of the sound signals.

7. The sound processing method as claimed in claim 5, wherein the sound signals x(n) include the harmonic region h(n) and the noise region w(n) as defined by:

$$x(n)=h(n)+w(n).$$

8. The sound processing method as claimed in claim 5, wherein the noise reduced signals include the harmonic region h(n) and a noise region w(n) as defined by $$\bar{x}=K(h+kw)\equiv KX,$$

wherein X denotes an optimal restraint index, and k denotes a noise restraint index.

9. The sound processing method as claimed in claim 5, wherein the first and second constraints are applied to the sound signals in the form of vector as defined by $$\bar{x}^T\bar{x}=x^Tx,(x-\bar{x})^T(x-\bar{x})=\beta x^Tx$$

And arranged as represented by $$\bar{x}^T x=\left(1-\frac{\beta}{2}\right)x^T x,$$

so that the noise restraint index defined by $$K=\left(1-\frac{\beta}{2}\right)\frac{x^T x}{X^T x},$$
$$\bar{x}=KX,$$

Is obtained, and wherein β is a constant less than 1.

10. A sound processing apparatus, comprising:

a sound signal input unit for receiving sound signals;

a harmonic noise separator for repeatedly performing an amplification of a harmonic region and a reduction of a noise region in the received sound signals, and separating the harmonic region and the noise region until an energy difference between two continuous harmonic components is below a preset threshold value which is already set, while separating the harmonic region and the noise region when the energy difference between the two continuous harmonic components is lowered below the preset threshold value; and a noise restrainer for restraining the separated noise region depending on a predetermined noise restraint index k so as to output noise attenuated signals, wherein the noise attenuated signals are obtained using first and second constraints which respectively assume that signals have substantially the same energy both before and that after noise is processed, and signals after noise is processed are substantially identical to signals before the noise is processed.

11. The sound processing apparatus as claimed in claim 10, wherein the harmonic noise separator comprises:

a harmonic region estimation section which extracts information relating to cepstrum and pitch, so as to estimate the harmonic region;

a harmonic noise separation iteration section for repeatedly performing an amplification of the harmonic region and a reduction of the noise region;

an estimation section for the harmonic noise separation for providing the harmonic noise separation iteration section with the ability to repeatedly perform an amplification of the harmonic region and the reduction of a noise region until an energy difference between two continuous harmonic components in the received sound signals which pass through the harmonic noise separation iteration section is less than the preset threshold value; and a harmonic noise separator for separating the harmonic region and the noise region from the sound signals which pass through the harmonic noise separation estimation section.

12. The sound processing apparatus as claimed in claim 11, wherein the harmonic noise separation iteration section comprises:

a harmonic extrapolation unit for setting a frequency domain value in the noise region to zero, and extrapolating current harmonic samples in the harmonic region into the noise region;

a noise estimation unit for subtracting the harmonic sample in the noise regions from an initial noise sample, and extrapolating the residual noise sample value into the harmonic region;

a noise extrapolation unit for setting a frequency domain value in the harmonic region to zero, and extrapolating current noise samples in the noise region into the harmonic region; and a harmonic estimation unit for subtracting the noise samples from the initial harmonic sample, and extrapolating the residual noise sample value into the harmonic region.

13. A sound processing method comprising the steps of:

repeatedly performing an amplification of a harmonic region and a reduction of a noise region in received sound signals until an energy difference between two continuous harmonic components is less than a preset threshold value;

separating the harmonic region and the noise region when the energy difference between the two continuous harmonic components is less than the preset threshold value after the amplification of the harmonic region and the reduction of the noise region are performed; and restraining the separated noise region depending on a predetermined noise restraint index k so as to output noise attenuated signals, wherein the noise attenuated signals are obtained using first and second constraints which respectively assume that signals have substantially the same energy both before and that after noise is processed, and signals after noise is processed are substantially identical to signals before the noise is processed.

14. A sound processing method comprising the steps of:

repeatedly performing an amplification of a harmonic region and a reduction of a noise region in received sound signals until an energy difference between two continuous harmonic components is less than a preset threshold value;

separating the harmonic region and the noise region when the energy difference between the two continuous harmonic components is less than the preset threshold value after the amplification of the harmonic region and the reduction of the noise region are performed; and restraining the separated noise region depending on a predetermined noise restraint index k so as to output noise attenuated signals, wherein separating the harmonic region and the noise region comprises:

estimating the harmonic region using information relating to cepstrum and pitch;

performing an amplification of the harmonic region and a reduction of the noise region;

determining, after the amplification of the harmonic region and the reduction of the noise region, if the energy difference between the two continuous harmonic components in the sound signals is less than the preset threshold value; and separating the harmonic region and the noise region from the sound signals when the energy difference between the two continuous harmonic components is the preset threshold value aider the determining step is performed.

15. The sound processing method as claimed in claim 14, further comprising performing the amplification of the harmonic region and the reduction of the sound region unless the energy difference between the two continuous harmonic components is less than the preset threshold value after the determining step is performed.

16. The sound processing method as claimed in claim 14, wherein the step of performing the amplification of the harmonic region and the reduction of the noise region comprises:

setting the frequency domain value in the noise region to zero, and extrapolating the current harmonic samples of the harmonic regions into the noise region;

subtracting the harmonic sample from the initial noise sample, and extrapolating the residual noise sample values into the harmonic region;

setting the frequency domain value of the harmonic region to zero, and extrapolating the current noise samples of the noise region into the harmonic region; and subtracting the noise sample of the harmonic regions from the initial harmonic sample, and extrapolating the residual harmonic sample values into the noise region.

* * * * *